(12) United States Patent
Zeng et al.

(10) Patent No.: US 12,072,329 B2
(45) Date of Patent: *Aug. 27, 2024

(54) SPATIAL SEPARATION OF PARTICLES IN A PARTICLE CONTAINING SOLUTION FOR BIOMEDICAL SENSING AND DETECTION

(71) Applicant: Instrumentation Laboratory Company, Bedford, MA (US)

(72) Inventors: Hansong Zeng, Acton, MA (US); Gert Blankenstein, Cambridge, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/791,734

(22) Filed: Oct. 24, 2017

(65) Prior Publication Data

US 2018/0052147 A1 Feb. 22, 2018

Related U.S. Application Data

(62) Division of application No. 14/992,284, filed on Jan. 11, 2016, now Pat. No. 11,959,907.

(Continued)

(51) Int. Cl.
*G01N 33/49* (2006.01)
*B01L 3/00* (2006.01)
(Continued)

(52) U.S. Cl.
CPC ........ *G01N 33/49* (2013.01); *B01L 3/502715* (2013.01); *B01L 3/502761* (2013.01);
(Continued)

(58) Field of Classification Search
CPC .............. G01N 33/491; G01N 33/5002; B01L 2400/0436; B01L 2400/0439
See application file for complete search history.

(56) References Cited

U.S. PATENT DOCUMENTS 4,854,170 A 8/1989 Brimhall et al.
5,902,489 A * 5/1999 Yasuda ................ B01D 21/283
204/660

(Continued)

FOREIGN PATENT DOCUMENTS

AU 2016206974 B2 10/2018
CN 102257418 A 11/2011
(Continued)

OTHER PUBLICATIONS

Nam, J. et al. "Separation of platelets from whole blood using standing surface acoustic waves in a microchannel," Lab Chip, 2011, 11, 3361-3364. (Year: 2011).*

(Continued)

*Primary Examiner* — Jennifer Wecker
*Assistant Examiner* — Michelle Adams
(74) *Attorney, Agent, or Firm* — ArentFox Schiff LLP

(57) ABSTRACT

A device and method for analyte detection and analytes in a particulate bearing fluid such as whole blood having an instrument for partitioning the particles from the fluid that is integrated with a detector for analyses of one or more particulate bearing fluid analytes while the particles in the particulate bearing fluid are partitioned.

16 Claims, 6 Drawing Sheets

Related U.S. Application Data

(60) Provisional application No. 62/102,308, filed on Jan. 12, 2015.

(51) Int. Cl.
*G01N 1/40* (2006.01)
*G01N 33/50* (2006.01)

(52) U.S. Cl.
CPC ......... *G01N 1/4077* (2013.01); *G01N 33/491* (2013.01); *B01L 2200/0647* (2013.01); *B01L 2300/06* (2013.01); *B01L 2300/0654* (2013.01); *B01L 2300/0816* (2013.01); *B01L 2300/0861* (2013.01); *B01L 2300/0864* (2013.01); *B01L 2400/0436* (2013.01); *B01L 2400/0439* (2013.01); *G01N 33/5002* (2013.01)

(56) References Cited

U.S. PATENT DOCUMENTS

| | | | |
|---|---|---|---|
| 7,003,153 | B1 | 2/2006 | Kerofsky |
| 7,484,414 | B2* | 2/2009 | Priev .................. G01N 15/06 210/748.05 |
| 8,846,408 | B2 | 9/2014 | Ward et al. |
| 8,865,003 | B2 | 10/2014 | Yang |
| 9,494,570 | B2 | 11/2016 | Bransky et al. |
| 9,656,263 | B2 | 5/2017 | Laurell et al. |
| 9,656,265 | B2 | 5/2017 | Adolfsen et al. |
| 9,921,147 | B2* | 3/2018 | Aubert ................. G01N 21/03 |
| 11,231,409 | B2* | 1/2022 | Bosy ................. G01N 21/3151 |
| 11,327,048 | B2 | 5/2022 | Irving et al. |
| 2005/0106064 | A1 | 5/2005 | Laurell et al. |
| 2005/0158704 | A1* | 7/2005 | Tyvoll ................. A61B 5/14532 435/4 |
| 2011/0207238 | A1* | 8/2011 | Horii ................. B01L 3/502761 422/69 |
| 2012/0214224 | A1 | 8/2012 | Chan |
| 2012/0218541 | A1 | 8/2012 | Barrett et al. |
| 2013/0043170 | A1 | 2/2013 | Rose et al. |
| 2013/0104369 | A1 | 5/2013 | Alferness |
| 2013/0156644 | A1 | 6/2013 | Lee et al. |
| 2014/0008307 | A1* | 1/2014 | Guldiken ............ B01L 3/502761 422/502 |
| 2014/0231315 | A1 | 8/2014 | Laurell et al. |
| 2014/0273858 | A1 | 9/2014 | Panther et al. |
| 2014/0305196 | A1 | 10/2014 | Ellis |
| 2014/0336062 | A1 | 11/2014 | Graves et al. |
| 2015/0253226 | A1 | 9/2015 | Augustsson et al. |
| 2015/0308971 | A1 | 10/2015 | Bisgaard |
| 2016/0202237 | A1 | 7/2016 | Zeng et al. |
| 2017/0010210 | A1 | 1/2017 | Choung |
| 2018/0049686 | A1 | 2/2018 | Marchiarullo et al. |
| 2018/0052147 | A1 | 2/2018 | Zeng et al. |
| 2018/0106720 | A1 | 4/2018 | Schonbrun et al. |
| 2022/0091068 | A1 | 3/2022 | Irving et al. |

FOREIGN PATENT DOCUMENTS

| | | |
|---|---|---|
| DE | 102004013960 | 8/2005 |
| DE | 102004013960 A1 | 8/2005 |
| EP | 3245001 A1 | 4/2021 |
| JP | 2000-199744 A | 7/2000 |
| JP | 2001/258868 | 9/2001 |
| JP | 2008/051824 | 3/2008 |
| JP | 2008/134063 | 6/2008 |
| WO | 1996017243 A1 | 6/1996 |
| WO | 2005/089082 | 9/2005 |
| WO | 2005089082 | 9/2005 |
| WO | 2010038230 A1 | 4/2010 |
| WO | 2011006525 A1 | 1/2011 |
| WO | 2013177560 A1 | 11/2013 |
| WO | 2014133451 | 9/2014 |
| WO | 2014178782 | 11/2014 |
| WO | 2014178782 A1 | 11/2014 |
| WO | 2016115014 A1 | 7/2016 |
| WO | 2018/065626 | 4/2018 |
| WO | 2018065626 A1 | 4/2018 |
| WO | 2020118018 A1 | 6/2020 |
| WO | 2020118021 A1 | 6/2020 |

OTHER PUBLICATIONS

Lenshof et al., "Accoustic Whole Blood Plasmapheresis Chip for Prostate Specific Antigen Microarray Diagnostic", Anal. Chem. 2009, 81, 6030-6037.

International Preliminary Report on Patentability, International Applicatiton No. PCT/US2016/012811, dated Jul. 18, 2017, pp. 1-6.

Final Office Action, U.S. Appl. No. 14/992,284, filed Dec. 22, 2017, dated Apr. 10, 2018, 12 pages.

Non-Final Office Action, U.S. Appl. No. 14/992,284, filed Dec. 22, 2017, 9 pages.

Japanese Office Action, Japanese Patent Application No. 2017-534914, mailed Mar. 6, 2019, 2 pages (translation included, 3 pages).

Examination Report issued in corresponding Canadian application No. 2,972,848, 4 pages.

Non-Final Office Action for U.S. Appl. No. 16/591,413, issued May 19, 2021, (19 pages).

Farkas et al. Thermochimica Acta, 2003, 404, pp. 141-148.

Henkelman et al. Materials Science and Engineering C 29 (2009) 1650-1654.

Jonsson et al. Ann Thorac Surg 2004, 78: 1572-1577.

Lenshof et al. "Acoustic Whole Blood Plasmapheresis Chip for Prostate Specific Antigen Microarray Diagnostic". Anal. Chem. 2009, 81, 6030-6037.

Final Office Action for U.S. Appl. No. 14/992,284, issued Jul. 16, 2021, (18 pages).

Final Office Action for U.S. Appl. No. 15/791,734, issued Dec. 28, 2020, (24 pages).

Non-Final Office Action for U.S. Appl. No. 15/791,734, issued Jun. 9, 2021, (25 pages).

International Preliminary Report on Patentability for International Patent Application No. PCT/US2019/054289, issued Apr. 15, 2021, 8 pages.

Christopher-John L Farrell et al.: "Serum indices: managing assay interference", Annals of Clinical Biochemistry., vol. 53, No. 5, Sep. 1, 2016, pp. 527-538, XP055652917, GB ISSN: 0004-5632, DOI: 10.1177/0004563216643557.

Elodie Sollier et al. Micro-scale blood plasma separation: from acoustophoresis to egg-beaters, Lab on a Chip, 2013,13, Issue 17, 1-24; doi: 10.1039/c3lc50432h.

Gossett et al. Label-free cell separation and sorting in microfluidic systems, Anal Bioanal Chem (2010) 397:3249-3267, DOI 10.1007/s00216-010-3721-9.

Chwee Teck Lim et al. Microfluidic Devices for Blood Fractionation, Micromachines 2011, 2, 319-343; doi:10.3390/mi2030319.

Tao Dong et al. Review: Recent Developments in Optical Detection Technologies in Lab-on-a-Chip Devices for Biosensing Applications, Sensors, 2014, 14, 15458-15479; doi:10.3390/s140815458.

Hun Lee et al. Review: Various On-Chip Sensors with Microfluidics for Biological Applications, Sensors 2014, 14, 17008-17036; doi: 10.3390/s140917008.

Examiner Requisition for Canadian patent application No. 2,972,848, issued Apr. 19, 2021, (9 pages).

Third Office Action for Chinese patent application No. 2016800056038, issued Oct. 30, 2020, with English translation, (14 pages).

Second Office issued in corresponding Chinese application No. 201680005603.8, dated Mar. 5, 2020 (No. of pp. 8), and English summary thereof (No. of pp. 3).

Examination Report issued in corresponding Canadian application No. 2,972,848, 5 pages.

Chinese Office Action issued in corresponding Chinese application No. 2016800056038, dated Jul. 8, 2019, and English translation thereof, 12 pages.

(56) References Cited

OTHER PUBLICATIONS

Communication pursuant to Article 94(3) EPC issued in European Patent Application No. 16 703 385.1, mailed Jun. 25, 2019, 5 pages.
Australian Examination Report issued in Australian Patent Application No. 2018236886, mailed Jul. 8, 2019, 3 pages.
Canadian Office Action for Canadian Patent Application No. 2,972,848 dated Oct. 22, 2018, 4 pages.
Manneberg, "Flow-free Transport of Cells in Microchannels by Frequency-modulated Ultrasound", The Royal Society of Chemistry, 2009, vol. 9, pp. 833-837.
Final Rejection issued on Sep. 5, 2018 in U.S. Publication No. 2018/0052147, 14 pages.
Japanese Office Action, Application No. 2017-534914, dated Jul. 9, 2018, 9 pages (includes both English and Japanese language versions).
Non-Final Rejection issued on Feb. 15, 2018 in the US pub. 20180052147; 9 pgs.
International Preliminary Report on Patentability, Dated Jul. 18, 2017, International Application No. PCT/US2016/012811, pp. 1-6.
International Search Report and Written Opinion for International Application No. PCT/US2016/012811, mailed on Apr. 15, 2016, 11 pages.
De Sarabia et al., "Application of high-power ultrasound to enhance fluid/solid particle separation processes," *Ultrasonics*, 38:642-646 (2000).
Jönsson et al., "Particle Separation Using Ultrasound Can Radically Reduce Embolic Load to Brain After Cardiac Surgery," *Ann Thorac Surg.*, 78:1572-1577 (2004).
Adams et al., "High-throughput, temperature-controlled microchannel acoustophoresis device made with rapid prototyping," *J. Micromech. Microeng.*, 22:1-8 (2012).
Chen et al., "Standing surface acoustic wave (SSAW)-based microfluidic cytometer," *Lab Chip*, 14:916-923 (2014).
Laurell, "Chip integrated strategies for acoustic separation and manipulation of cells and particles," *Chem. Soc. Rev.*, 36:493-506 (2007).
Petersson, et al., "Separation of lipids from blood utilizing ultrasonic standing waves in microfluidic channels," *Analyst*, 129:938-943 (2004).
Fourth Office Action for Chinese patent application No. 2016800056038, Issued Jul. 20, 2021, (17 pages).
Fifth Office Action for Chinese patent application No. 2016800056038, issued Dec. 9, 2021, with English Summary, (14 pages).
Examiner Requisition for Canadian patent application No. 2,972,848, issued Nov. 3, 2021, (14 pages).
Non-Final Office Action for U.S. Appl. No. 14/992,284, issued Feb. 23, 2021, (12 pages).
Communication pursuant to Rule 114(2) EPC for European Application No. 16703385.1, mailed Dec. 8, 2022, (21 pages).
Article "Non-destructive, non-contact handling method for biomaterials in micro-chamber by ultrasound", Sensors and Actuators B 64 (2000), pp. 128-135.
English machine translation of AI (JP 2000-199744 A), as supplied by Espacenet.
Additional English machine translation of AI •(JP 2000-199744 A), as supplied by Patent Translate (description only).
Non-Final Office Action for U.S. Appl. No. 17/560,828, issued Aug. 4, 2022, (7 pages).
Final Office Action for U.S. Appl. No. 14/992,284, issued Aug. 12, 2022, (13 pages).
Extended European Search Report in EP Application No. 23164469.1 dated Jun. 12, 2023 (11 pages).
Non-Final Office Action in U.S. Appl. No. 17/560,828 dated Jul. 19, 2023 (11 pages).
Examination Report No. 1 in AU Application No. 2022201391 dated Apr. 24, 2023 (4 pages).
Communication pursuant to Article 94(3) EPC for European patent application No. 16703385.1, issued Feb. 8, 2023, (5 pages).
Examination Report No. 2 for Australian Application No. 2022201391 dated Jan. 29, 2024, 5 pages.
Summons to attend oral proceedings pursuant to Rule 115(1) EPC in EP Application No. 16703385.1 dated Nov. 3, 2023, 6 pages.

\* cited by examiner

SPATIAL SEPARATION OF PARTICLES IN A PARTICLE CONTAINING SOLUTION FOR BIOMEDICAL SENSING AND DETECTION

RELATED APPLICATIONS

This application is a divisional of co-pending U.S. application Ser. No. 14/992,284 filed on Jan. 11, 2016, and claims priority to and benefit of U.S. Provisional application No. 62/102,308 filed Jan. 12, 2015, the content of which is incorporated by reference herein in its entirety.

FIELD OF THE INVENTION

The invention is generally related to a device and method for partitioning particles from a particle-containing fluid to obtain a substantially particle-free fluid for biomedical testing. More specifically, the invention is related to a device and method for measuring analytes in body fluids, for example, plasma or serum, more specifically, analytes in whole blood. In particular, the device and method are directed to arresting flow of whole blood in a microchannel of a microfluidic device and detecting analytes in the body fluid, such as whole blood, using acoustic partitioning of red blood cells from plasma in the whole blood at a detection region in the microchannel, and detecting the analyte in the detection region by an analyte detector, for example, an optical detector. More specifically, the method and device is useful for monitoring hemolysis in whole blood using acoustic partitioning of red blood cells at the detection region in combination with detection of free hemoglobin in the detection region while the whole blood in the microchannel is flowing or arrested.

BACKGROUND OF THE INVENTION

Systems for analysis of analytes in whole blood typically require collection of the fluid portion of whole blood, i.e., plasma, in a chamber, from the cellular portion of whole blood, principally red blood cells. Typically, before analysis, plasma is collected from the whole blood sample by centrifugation or filtering of whole blood to separate the cellular portion and collect the fluid, i.e., plasma portion which is then introduced into an analyzer for detection of the analyte of interest. The separation of particles or cells from complex fluid mixtures is an essential tool in not only in clinical diagnostics relevant to healthcare, but also in many areas of biological research and medicine.

Microfluidics, a technology in which microchannels are in the diameter range of 10 nanometers to less than 1.5 millimeters, offer great potential for many high performance cell-sorting applications described in the art. Microfluidics allow precise manipulation of the separation forces that govern movement of cells. A number of different force fields have been successfully utilized within microchannels to sort cells including hydrodynamic focusing, magnetic separation/sorting and acoustophoretic cell separation/sorting devices, such as surface acoustic waves and ultrasonics.

Notwithstanding the cell separation techniques in the prior art, an unmet challenge in clinical medicine is the development of a device and methods in point-of-care applications for the high throughput and rapid measurement of analytes in body fluids such as whole blood without the need for filtering or centrifuging whole blood to collect plasma from the cellular portion, and then introducing the collected plasma into an analyzer for analysis of collected plasma for the analytes of interest. The additional time, hardware, human operation procedures necessary to filter and centrifuge whole blood to collect plasma for analysis markedly reduces throughput, and increases the risk of device malfunction and human error.

An additional unmet challenge in clinical diagnostics, is the development of a rapid test to detect the presence of hemolysis in a whole blood sample to ensure that the measurement of a target analyte is not skewed by the release of analytes from damaged red blood cells (RBCs). Hemolysis may be detected by the measurement of hemoglobin, a protein normally located only within red blood cells but is released when red blood cells are damaged. Detecting free hemoglobin in a blood sample, i.e., hemolysis, indicates whether or not the analyte concentration in a blood sample is skewed by the release of analytes from damaged red blood cells.

For example, in whole blood, potassium levels are usually about 4.0 mM, while potassium concentration within red blood cells is usually about 150 mM. In the course of collecting and handling whole blood from a patient, some cells, red blood cells in particular, may be physically damaged causing rupture of the red blood cells. When hemolysis occurs in a whole blood sample, the contents of the red blood cells are released and intermixed with the contents of the cell-free portion of whole blood, i.e., plasma, or in some cases, serum. Hemoglobin, a constituent of whole blood normally found within red blood cells, and other intracellular elements, e.g., potassium, are released from the intracellular compartment of damaged red blood cells into the fluid portion of blood, i.e., plasma or serum.

Because the concentration of potassium within red blood cells is 25-75 times higher than the concentration of potassium in normal plasma, measuring potassium in the fluid portion of a patient's hemolyzed blood sample will induce an artifact, such as an elevation of the patient's actual plasma potassium level. The potassium concentration in the fluid portion of non-hemolyzed blood is an important indicator of numerous conditions. An over-estimate of the concentration of potassium in hemolyzed blood may result in treatment of the patient for hyperkalemia (increased blood potassium) when the patient may actually have low or normal concentration of potassium in the patient's non-hemolyzed blood sample. Unfortunately, only a relatively small number of ruptured red blood cells can result in an artificially elevated blood potassium level.

In addition to elevated plasma potassium, when a blood sample is hemolyzed, other analytes such as lactate dehydrogenase, acid phosphatase, aspartate aminotransferase, and alanine aminotransferase, for example, are also present in higher concentration in red blood cells than in the fluid portion of blood, and these analytes may be artificially elevated in hemolyzed blood. Currently, hemolysis accounts for about 3.3% of invalid clinical laboratory testing.

Current methods for detecting analytes such as hemoglobin in a whole blood sample to detect hemolysis include centrifuging the whole blood sample to remove cells and collect plasma, with the volume of tens of milliliters of whole blood in a closed tube configuration, or filtering the whole blood sample to remove red blood cells, and collect plasma, then transferring the collected plasma to a detector apparatus, an optical detector, for example, to apply methods to analyze the collected plasma for the target analyte of interest. For example, for the detection of hemolysis, the blood sample is centrifuged to collect plasma, plasma is transferred to an optical detector apparatus, and methods, e.g. Roche Index Factor, are used to determine the presence of free extra-cellular hemoglobin in the plasma portion.

Notably, no current methods exist that operate on whole or non-filtered or non-centrifuged blood to determine hemolysis.

Acoustic waves generated by various mechanisms, including ultrasound waves, surface acoustic waves, and bulk acoustic waves, are currently used to manipulate particles suspended in complex liquid mediums, such as whole blood, to concentrate and collect the particles, such as red blood cells, white blood cells, and platelets, while the complex liquid medium is flowing continuously in a microchannel. Each of the particle-concentrated portions and/or or the particle-free or particle-diluted portions of the complex liquid medium are collected separately.

For example, as shown in FIG. 1, the use of ultrasonic standing wave across the lateral direction of the microchannel to separate particles from a whole blood sample has been described. An acoustic standing wave of a half wavelength is maintained within the microchannel as the particles are moving through the field, causing the particles to migrate to the pressure node at the center of the microchannel. A particle-diluted/free portion of the sample continues to flow and is collected through the outlets on the two sides of the microchannel, while the particle-concentrated portion of the sample is collected through the outlet along the center of the microchannel.

Alternatively, as shown in FIG. 2, ultrasonic standing wave applied along the vertical direction of a microchannel to separate red blood cells from flowing whole blood has been described. The RBCs in the flowing whole blood are driven to the upper portion of the fluid in the microchannel, while the plasma continues to flow to the bottom portion of the microchannel. By placing two outlet ports in the top and bottom sides of the flow device respectively, the plasma or RBCs are each collected separately from the apparatus.

SUMMARY OF THE INVENTION

One objective of the present invention is to provide a system and method for analyzing analytes in a complex particulate bearing fluid such as whole blood in which partitioning of the particulate material, such as red blood cells, from the fluid, such as plasma, occurs in the same system as detection of analytes in the complex particulate bearing fluid. In other words partitioning of blood cells from plasma in whole blood occurs in the same device of the system, such as a microchannel, in which analytes in the partitioned flowing or arrested plasma are detected by a detector.

In one aspect, the invention disclosed herein is directed to a system for analyzing analytes in a complex particulate bearing fluid. The complex particulate bearing fluid comprises a fluid portion and a particulate portion, e.g., whole blood having plasma and red blood cells, respectively. The system comprises a microchannel capable of housing a column of the complex particulate fluid. The microchannel has at least one analyte detection region and an acoustic transducer region. An acoustic transducer in the acoustic transducer region generates acoustic waves and is aligned with the at least one analyte detection region in the microchannel. Acoustic waves generated by the acoustic transducer partition the particulate portion from the fluid portion of the column of complex particulate fluid in the microchannel. An analyte detector is located in the analyte detection region of the microchannel for measuring a target analyte of interest in the fluid portion of the complex particulate fluid.

In one embodiment, the system according to the invention includes a fluid flow arrestor for arresting flow of the complex fluid at the analyte detection region and/or a fluid collector for collecting particulate free fluid or reconstituted complex particulate fluid after analysis of the target analyte. The particulate free fluid or the reconstituted complex particulate fluid collector comprises, for example, a microchannel, a pocket, a dilatation, a chamber, or a cavity.

The acoustic waves are selected from the group consisting but not limited to ultrasonic standing waves, surface acoustic wave, bulk acoustic wave, and acoustic waves with frequency preferably in the range of 2 kHz to 2 GHz.

The system according to the invention may comprise one or more than one acoustic transducers, such as two, three, 4-6 or more, and one or a plurality of analyte detectors, such as two, three, 4-6 or more, and one or more than one analyted detector, such as two, three, 4-6 or more analyte detector. Typically, but not always, there are as many acoustic regions in the microchannel as there are acoustic transducers. Typically, but not always, there are as many detector regions in the microchannel as there are detectors.

In another aspect, the invention is a method for analyzing an analyte in whole blood. A sample of whole blood is introduced into a microchannel of an analytical system according to the invention described herein. An acoustic transducer applies acoustic forces to the whole blood sample at an acoustic region of the microchannel. The acoustic forces partition the blood cells from the plasma of the blood. A detector is applied to the plasma in a detection region of said microchannel to analyze at least one analyte in the whole blood sample at the detection region.

In an embodiment of the method, the flow of plasma is arrested at the detection region by a flow arrestor and the detector detects the target analyte while the plasma flow is arrested at the detection region. Alternatively, the flow of whole blood and plasma is not arrested and the detector detects the analyte of interest while plasma is flowing through the detection region.

An additional feature of the method of invention may include collection of plasma or collection of reconstituted whole blood in a collector such as a microchannel, a pocket, a dilatation, a chamber, or a cavity downstream from the acoustic force. Reconstituted whole blood is formed by releasing the acoustic forces applied by the acoustic transducer on the fluid in the microchannel to enable the red blood cells that were partitioned from plasma to remix with the plasma to reconstitute whole blood. The reconstituted whole blood may be used for additional clinical analyses.

These and other objects, features and advantages of the present invention disclosed herein, as well as the invention itself, will be more fully understood from the following description of preferred embodiments and claims, when read together with the accompanying drawings. The drawings are not necessarily to scale, emphasis instead being placed upon illustrating the principles of the invention. Furthermore, it is to be understood that the features of the various embodiment described herein are not mutually exclusive and can exist in various combinations and permutations.

The drawings are not necessarily to scale, emphasis instead generally being placed upon illustrating the principles of the invention.

DESCRIPTION OF THE INVENTION

Figure 1A:
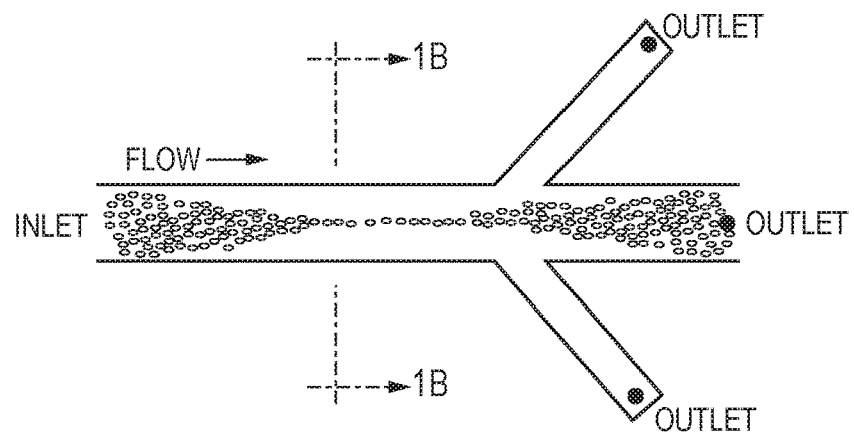
FIG. 1A schematically illustrates a prior art device and acoustic configuration for separating particles in a whole blood sample by the use of ultrasonic standing waves applied perpendicular to the long axis of a channel.
Figure 1B:
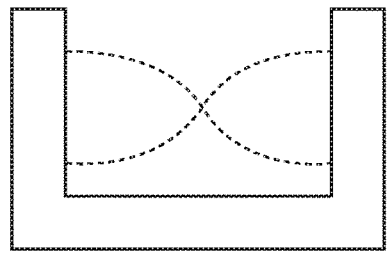
FIG. 1B schematically illustrates a cross-sectional view at 1B-1B of the acoustic force of the system illustrated in FIG. 1A.
Figure 2:
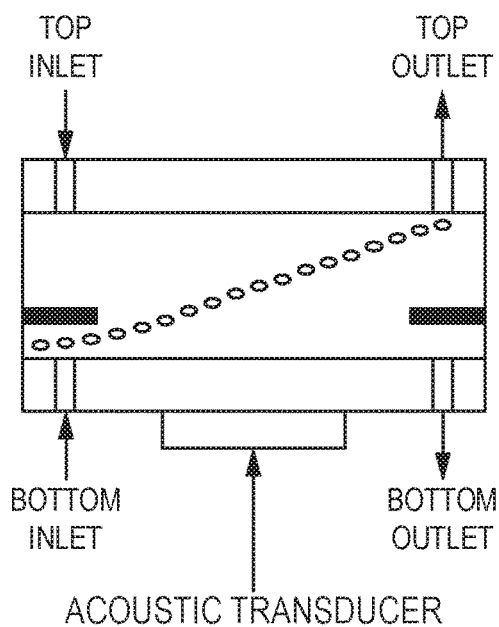
FIG. 2 illustrates another prior art device for separating particles in a whole blood sample by the use of ultrasonic standing waves applied along the vertical direction of a channel.

The invention described below is directed to a system and a method for detecting and measuring analytes in whole blood by integrating a microfluidic device, acoustic transducers and a detection apparatus for a wide range of needs for analyzing analytes in a complex fluid, such as whole blood and other fluids, that include particles in the size range of a few nanometers to hundreds of microns. Target analytes include but are not limited to glucose, lactate, sodium, potassium, chloride, hemoglobin, troponin I, cholesterol, and coagulation factors.

The invention disclosed herein has at least the following advantages over existing systems for detecting and measuring analytes in whole blood including but not limited to, free hemoglobin. Hemoglobin may be used as an indicator of hemolysis in the blood sample undergoing analysis.

- a one step, single integrated device for enhanced particulate partitioning efficiency in a particulate-bearing fluid by application of a continuous acoustic force in a localized area of the fluid while flow is arrested, or alternatively, while fluid is flowing and measuring an analyte by a detector in the fluid from which the particles are partitioned from the arrested or flowing fluid;
- one step partitioning of particulates and fluid in a flowing or arrested sample, i.e., single stage partitioning of particles, e.g., cells, and no need for multi-stage separation that is used for "separation while flowing";
- elimination of a separate device, for example, a centrifuge or filters to collect plasma for analytical measurement, or a separate analyte detection device into which the collected plasma is analyzed;
- reversibility of partitioned particles, e.g., red blood cells (RBCs), to reconstitute whole blood thereby maintaining blood integrity, e.g., hematocrit, blood constituents, RBC integrity, after application of acoustic forces and after analyte analysis;
- reusability of the whole blood sample (because of particulate partitioned reversibility) without the need for additional remixing of plasma and RBCs for other whole blood measurements, e.g., whole blood viscosity;
- small sample volume required for analysis in a range of 1 microliter to 10 milliliters;
- simplicity of manufacture and operation of acoustics, fluidics, and detectors, e.g., optical detectors in the microfluidic device according to the invention.

A significant advantage of the invention disclosed herein is a device and method for the partitioning of plasma from a whole blood sample, analyte detection in the sample in one step: no need to collect plasma first and then perform analysis on collected plasma. In a microchannel, plasma is reversibly separated and not collected from the cellular content of whole blood. The separated plasma is analyzed in an integrated detector without a collecting step or a step requiring collected plasma analysis in a separate independent clinical analyzer for the analyte of interest.

As used herein, a particle refers to any particulate matter in a size range from 10 nm to 1.5 millimeters including but not limited to cells such as red blood cells, white blood cells, platelets, bacteria, viruses and other pathogens.

A particular non-limiting application of the disclosed system for analysis of a complex particle-bearing fluid pertains to clinical diagnostics in the field of healthcare. For example, the invention described herein eliminates the need for centrifuging or filtering a patient's whole blood sample to achieve plasma separation and plasma collection in a container other than the microchannel in which a whole blood sample is held. The system according to the invention improves sample throughput by eliminating the requirement for additional instrumentation, e.g., an independent detector in a clinical analyzer, or centrifuge in the point-of-care environment such as in the emergency, cardiac care, or critical care room, or in military hospitals in the field.

Figure 3A:
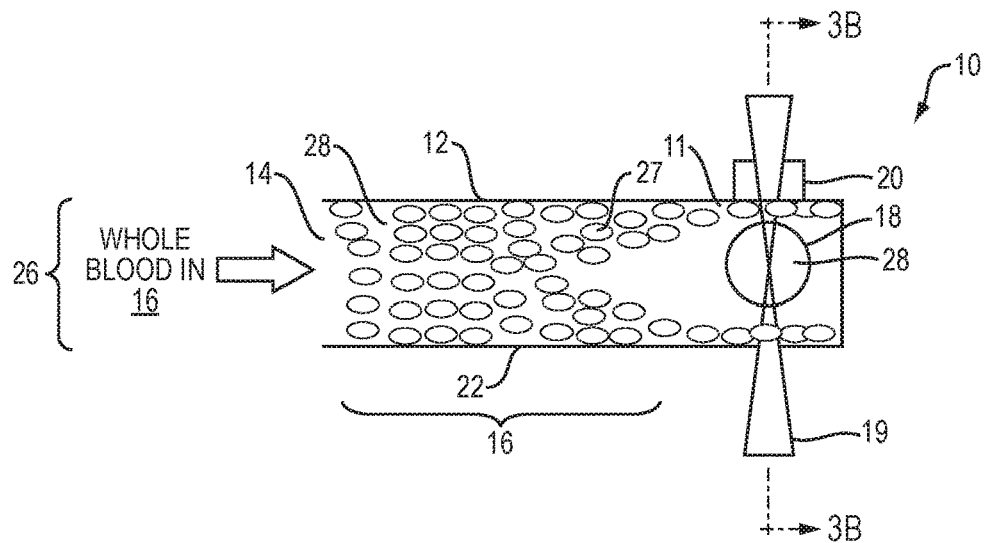
FIG. 3A schematically illustrates one embodiment of an acoustic configuration of a system according to the invention for detecting an analyte in a particle containing fluid in a channel by an integrated detector while the particles are partitioned from the fluid towards the wall of the microchannel.
Figure 3B:
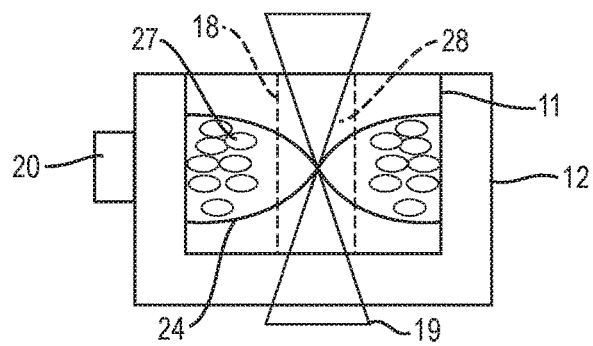
FIG. 3B schematically illustrates a cross-sectional view at 3B-3B of the acoustic force of the system illustrated in FIG. 3A applied to a column of blood for partitioning the red blood cells from the plasma.

According to the invention, and referring to one embodiment illustrated in FIG. 3A-3B, the system 10 includes a microfluidic device that accepts a particulate-bearing fluid, e.g., a whole blood sample into a microchannel 12 having a diameter in the range of, for example, about 50 nm to 1.5 mm An acoustic transducer 20, or a pair of acoustic transducers 20a, 20b or an array of acoustic transducers 20n, integrated in the system 10, generates acoustic forces 24 which are applied transversely to a stationary (arrested) or flowing column 26 of whole blood in the microchannel 12. Acoustic forces 24 generated by acoustic transducers 20n include but are not limited to ultrasound waves, surface acoustic waves, bulk acoustic waves, etc., with the frequency in the range of about 2 KHz to 2 GHz. The acoustic forces partition the red blood cells (RBCs) 27 from the plasma 28 (due to distinct physical properties of plasma and RBCs) in the microchannel 12. While the red blood cells 27 are partitioned in the fluid column 26 in the microchannel 12, the plasma 28 in the whole blood sample is analyzed by an integrated detector 19 such as an optical apparatus or sensors, for the target analyte of interest, for example, hemoglobin. Because the measurement is done by the detector 19 while the column 26 of whole blood sample is partitioned into plasma 28 in one portion of the column 26 and cells 27 in another portion of the column 26 in the flow microchannel 12, the system 10, according to the invention, has advantages over the prior art by eliminating the potentially high risk of operator contamination, and the otherwise necessary throughput-limiting step of first centrifuging or filtering whole blood to collect plasma for analysis that is performed in a separate clinical analyzer apparatus.

In a particular embodiment, an arrested flow mode, in contrast to a continuous flow method, enhances the efficiency of particulate partitioning and integration of an on-chip detection apparatus. In this embodiment, the system 10 according to the invention includes a fluid flow arrestor (not shown) for arresting the flow of fluid such as blood in the separation/detection microchannel 12 by hardware, such as but not limited to pumps, valves, flow regulators, compressors and processors (not shown) for a defined period of time while the acoustic force is applied to the arrested particulate bearing fluid sample in the microchannel 12. Arrested blood flow increases residence time of the sample in the applied acoustic field. Continuous separation of the particles in a designated area, i.e., a detection region of the microchannel, is achieved.

Additionally, by releasing the acoustic forces on the fluid sample, the partitioning of particles in the complex fluid medium is reversible, thereby reconstituting the particles, such as cells, in the complex fluid medium, such as plasma, to reconstitute whole blood for further analysis. The reconstituted whole blood may be captured in a collector positioned in fluid communication with the microchannel 12 in a reservoir such as but not limited to another microchannel, a pocket, a dilatation, a chamber, or a cavity. Thus, the system 10 according to the invention is readily applicable to point-of-care applications as well as in a central clinical laboratory.

Additionally, the system according to the invention 10 may be incorporated into the extracorporeal blood line of a heart/lung machine for continuous monitoring of blood analytes during a surgical procedure requiring cardiopulmonary bypass such as but not limited to cardiac valve repair or replacement, pulmonary thrombectomy, repair of septal defects, congenital cardiac or vascular defects, and thromboendarterectomy. The system according to the invention may be used in the extracorporeal blood line of infants with serious congenital defects receiving life support or to oxygenate blood to maintain patients in need of and waiting for an organ transplant.

In addition to detection of hemolysis, the system and method according to the invention can also be used in the following fields:
  particle based chemical assays using reporter beads, such as bead-based virus detection, or bacteria detection, for example
  other cell based assays using cell suspensions, such as detection of circulating tumor cells (CTC) in a blood sample, other body fluid samples, or cell fractions obtained from a tissue such as but not limited to a neoplasm Examples of the Various Embodiments of the System According to the Invention FIGS. 3A and 3B_illustrate the overall principle and one embodiment of the system 10 according to the invention for analysis of a complex particle-bearing fluid (complex fluid) 16 such as whole blood for a target analyte of interest. The system 10 includes a microfluidic device configuration 22 comprising one or more microchannels 12 and at least a sample port 14 in fluid communication with at least the one microchannel 12 for introducing the complex particle-bearing fluid 16. The microchannel 12 includes at least one detector 19 and at least one detection site 18 or region for detecting an analyte in the complex particle-bearing fluid 16. At least one acoustic transducer 20 is integrated in the microfluidic device 22 for transmitting acoustic waves 24 into the column 26 of the complex fluid 16, whole blood, for example, in the detector region 18 of the microchannel 12. Acoustic forces 24 applied to the detector region 18 of the fluid column 16 partition the particles 27 in the complex fluid 16, RBCs 27, for example, and generate a substantially particle-free fluid 28, plasma for example, in the detector region 18 for analysis of the target analyte by the detector 19.

Figure 3C:
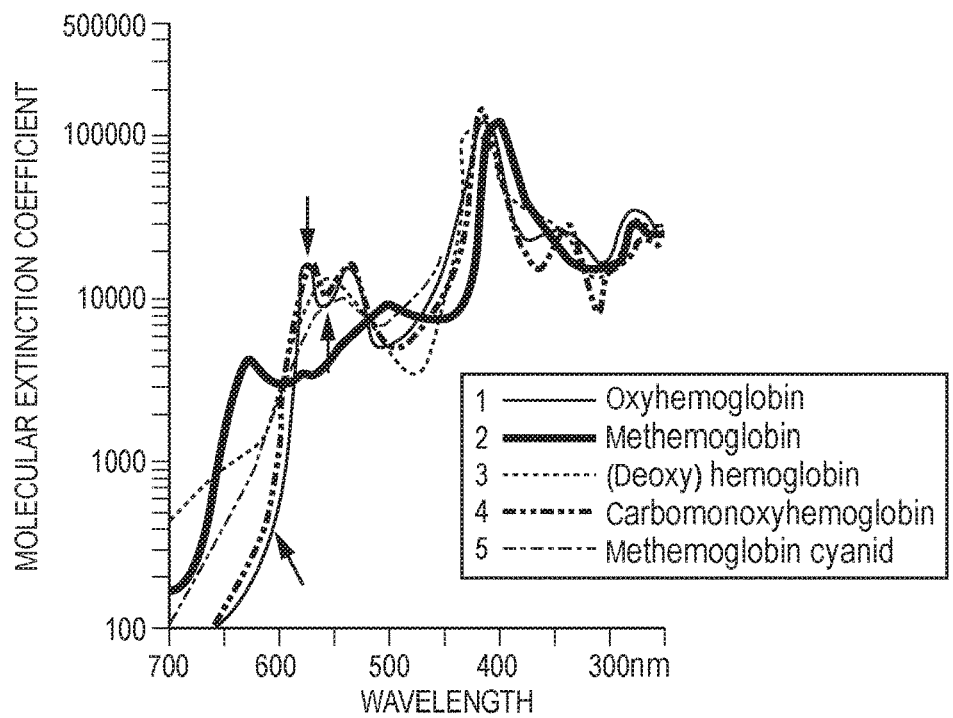
FIG. 3C is a graph plotting molecular extinction coefficients versus wavelength for oxyhemoglobin, methemoglobin, (Deoxy)monoxyhemoglobin, carboxyhemoglobin, and methemoglobin cyanid.

With continued reference to FIGS. 3A and 3B, detector 19 such as optical detectors/transmitters, or sensors such as traditional photometry detection apparatus, traditional fluorescence measurement systems, time resolved fluorescence measurement system, which usually includes LEDs, spectrometers, photodiodes and related optics, are integrated with the acoustic transducers 20 at the detector region 18 in the microchannel 12 for detection of the analyte of interest as shown in FIG. 3A. FIG. 3B is a cross-sectional view of an acoustic force 24 in the microchannel illustrated in FIG. 3A, according to the invention, moving RBCs 27 in the column 16 of whole blood to the sides 11 of the microchannel 12. Analysis by the detector 19 is performed on the substantially particle-free fluid 28 while flow is arrested or, alternatively, while the substantially particle-free fluid 28 is moving in the microchannel 12. Specifically for hemolysis (free hemoglobin detection), the optical absorption spectrum of hemoglobin in contrast to other blood constituents is illustrated in FIG. 3C.

As described above, by releasing acoustic forces on the fluid sample, the partitioning of RBCs is reversible permitting the reconstitution of whole blood that may be collected in a downstream collector such as, for example, a tube, vessel, bag, or chamber for collecting and holding whole blood.

Figure 4A:
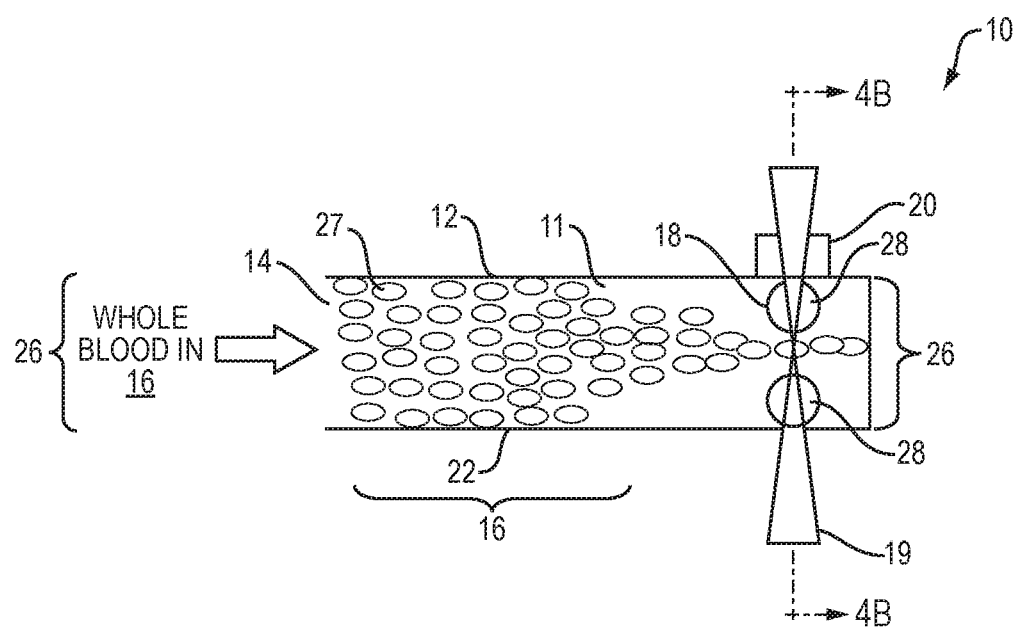
FIG. 4A schematically illustrates another embodiment of an acoustic configuration of the system according to the invention for detecting an analyte in a particle containing fluid in a channel by an integrated detector while the particles are partitioned from the fluid towards the center of the microchannel.
Figure 4B:
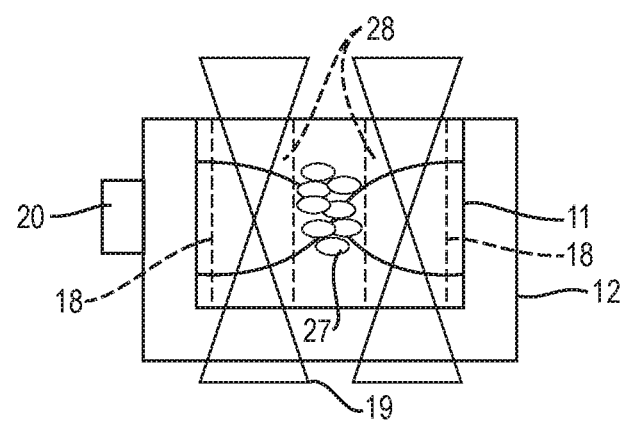
FIG. 4B schematically illustrates a cross-sectional view at 4B-4B of the acoustic force of the system illustrated in FIG. 4A applied to a column of blood. The red blood cells are partitioned from the plasma for detecting an analyte in the partitioned fluid.

FIGS. 4A-4B illustrate another embodiment of the acoustic configuration system 10 for particle partitioning RBCs from whole blood, for example, and generation of a substantially particle-free fluid for fluid analysis, plasma for example, for detection and analysis of a target analyte. The width of the microchannel 12 can be in the range of about 50 nm to 1.5 millimeters, preferably 5 micrometers to 1 millimeter, for example. The acoustic wave 24 used in this configuration could be ultrasonic waves, surface acoustic waves, bulk acoustic waves, for example, with the frequency in the range of 2 KHz to 2 GHz.

Detectors 19 such as optical detectors/transmitters, or sensors such as traditional photometry detection apparatus, traditional fluorescence measurement systems, time resolved fluorescence measurement system, which usually includes LEDs, spectrometers, photodiodes and related optics, are located at a detector region 18 in the microchannel 12 for detection of the analyte of interest.

In this embodiment, shown in FIG. 4A, the complex fluid 16 is introduced via a sample port 14 in fluid communication with a microchannel 12. The complex fluid 16 fills and forms a fluid column 26 within the microchannel 12. Acoustic transducers 20 and analyte detectors 19 are integrated at a detection region 18 in the microchannel for transmitting acoustic waves 24 into the column 26 of the complex fluid 16, column of whole blood for example, and for detection and analysis of a target analyte in the fluid column 26.

Analysis by the detector 19 is performed on the substantially particle-free fluid 28 while flow is arrested or, alternatively, while the substantially particle-free fluid 28 is moving in the microchannel 12. Detectors 19 including optical detectors/transmitters, or sensors such as traditional photometry detection apparatus, traditional fluorescence measurement systems, time resolved fluorescence measurement system, which usually includes LEDs, spectrometers, photodiodes and related optics, are integrated with the acoustic transducers 20 at the detector region 18 in the microchannel 12 for detection of the analyte of interest.

FIG. 4B is a cross-sectional view of RBCs 27 moved under the acoustic force 24 to the center of the microchannel 12 illustrated in FIG. 4A. The standing acoustic wave is introduced to the microchannel 12, and the acoustic force 24 moves the RBCs 27 to the center of the microchannel 12, leaving the areas close to the microchannel wall 11 with cell-free plasma 28. In this embodiment, the area close to the wall 11 can be used for analyte measurement.

As described above, by releasing acoustic forces on the fluid sample, the partitioning of RBCs is reversible permitting the reconstitution of whole blood that may be collected in a downstream collector such as, for example, a tube, vessel, bag or chamber for collecting and holding whole blood.

Figure 5A:
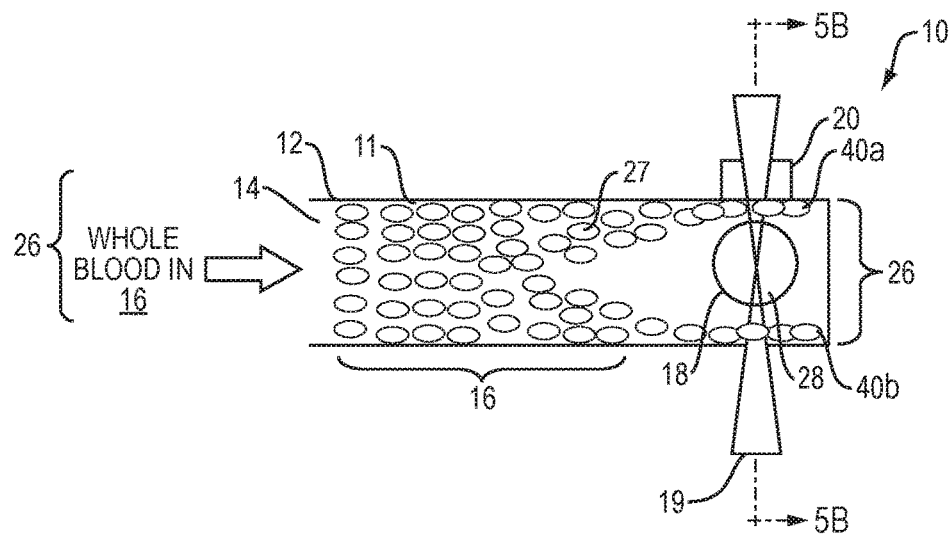
FIG. 5A schematically illustrates another embodiment of an acoustic configuration of the system according to the invention for detecting an analyte in a particle containing fluid in a channel by a detector. The detector is integrated with an acoustic transducer at a detection region while the particles are partitioned from the fluid.
Figure 5B:
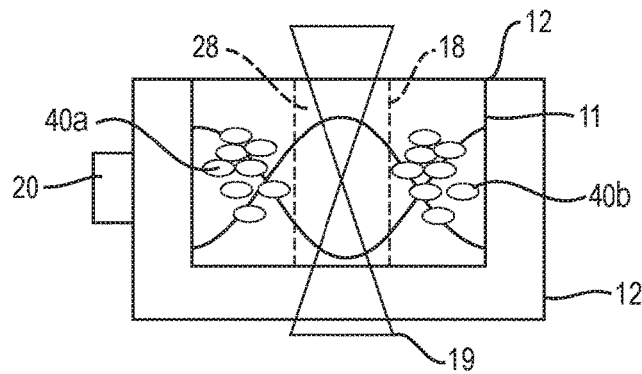
FIG. 5B schematically illustrates a cross-sectional view at 5b-5b of the acoustic force of the system illustrated in FIG. 5A applied to a column of blood. The red blood cells are partitioned from the plasma and an analyte may be detected in the partitioned fluid; one period of the applied standing wave introduced into the microchannel forms two pressure nodes moving the particles to the pressure nodes.

FIGS. 5A-5B illustrate another embodiment of the acoustic configuration 10 for particle partitioning, for example, RBCs in whole blood, and generation of a substantially particle-free fluid for fluid analysis, such as plasma, for detection and analysis of a target analyte.

In this embodiment, shown in FIG. 5A, the complex fluid 16 is introduced via a sample port 14 in fluid communication with a microchannel 12. The complex fluid 16 fills and forms a fluid column 26 within the microchannel 12. Acoustic transducers 20 and detectors 19 are integrated at a detection region 18 in the microchannel 12 for transmitting acoustic waves 24 into the column 26 of complex fluid 16, whole blood for example, and for detection and analysis of a target analyte in the fluid column 26.

Analysis by the detector 19 is performed on the substantially particle-free fluid 28 while flow is arrested or, alternatively, while substantially particle-free fluid 28 is moving in the microchannel 12.

FIG. 5B is a cross-sectional view of a microchannel 12 illustrated in FIG. 5A, showing the distribution of RBCs 27 inside the microchannel 12 in response to the acoustic force 24. In this embodiment, one period of the standing wave is introduced into the microchannel 12 forming two pressure nodes 40a, 40b in the fluid column 26. The RBCs 27 are moved to the pressure nodes 40a, 40b, leaving the area in the center 29 of the microchannel 12 and the areas next to the microchannel walls 11 with cell-free plasma 28.

The analyte detection is performed in the regions of cell-free plasma. The detector 19 such as optical detectors/transmitters, or sensors such as traditional photometry detection apparatus, traditional fluorescence measurement systems, time resolved fluorescence measurement system, which usually includes LEDs, spectrometers, photodiodes and related optics, are integrated with the acoustic transducers 20 at the detector region 18 in the microchannel 12 for detection of the analyte of interest.

As described above, by releasing acoustic forces on the fluid sample, the partitioning of RBCs is reversible permitting the reconstitution of whole blood that may be collected in a downstream collector such as, for example, a tube, vessel, bag or chamber for collecting and holding whole blood.

Figure 6:
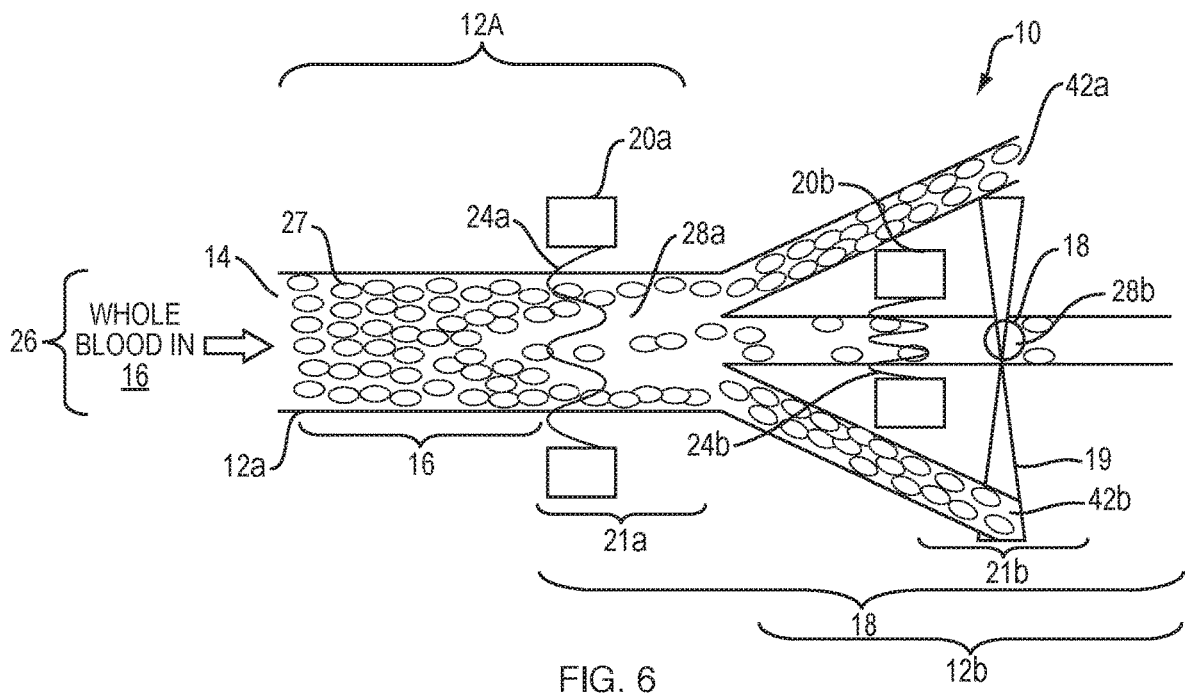
FIG. 6 schematically illustrates another embodiment of an acoustic configuration of the system according to the invention for detecting an analyte in a particle containing fluid in a channel by a detector located at a detector region of the channel and an acoustic transducer located at a first acoustic region in the channel and another acoustic transducer located at a second acoustic region in the channel.

FIG. 6 illustrates another embodiment of the acoustic configuration system 10 for particle partitioning, RBCs in whole blood, for example, and generation of a substantially particle-free fluid 28 for fluid analysis, such as plasma, for detection and analysis of a target analyte.

In this embodiment, the complex fluid 16 is introduced via a sample port 14 in fluid communication with a microchannel 12. The complex fluid 16 fills and forms a fluid column 26 within the microchannel 12. Acoustic transducers 20a and 20b are located at acoustic regions 21a, 21b, respectively for transmitting acoustic waves 24a, 24b, respectively into the column of the complex fluid 16, whole blood for example.

RBCs are moved by acoustic forces 24a towards the walls 11 of the microchannel 12. As the fluid flows further down the microchannel 12, the RBCs partitioned by acoustic forces 24a move out of microchannel 12 into one or more particle outlet channels 42a, 42b (42n). As illustrated in FIG. 6, a first and second microfluidic microchannel 12a, 12b, respectively are configured in serial. The first and second microchannels 12a, 12b have a first or second acoustic region 21a, 21b comprising a first and second acoustic transducer 20a, 20b, respectively.

After generation of a first substantially particle-free fluid 28a by partitioning the particles 27 in the first microchannel 12a at the first acoustic region 21a, by the application of an acoustic force 24, a substantially particle free portion flows into the second microchannel 12b and the particles are further partitioned from the fluid column 26 by the second acoustic transducer 20b in the second acoustic region 21b of the second microchannel 12b. In this embodiment of the system 10, the particles in the complex fluid such as whole blood are further partitioned by acoustic forces 24b in the second acoustic region 21b to obtain a further substantially particle-free fluid, such as plasma, for detection and analysis of a target analyte. Analysis by a detector 19 is performed on the second particle-free fluid 28b in the detector region 18 while the fluid is flowing or arrested after passing through the first acoustic region 21a and second acoustic region 21b.

Detector 19 such as optical detectors/transmitters, or sensors such as traditional photometry detection apparatus, traditional fluorescence measurement systems, time resolved fluorescence measurement system, which usually includes LEDs, spectrometers, photodiodes and related optics, are located in a detector region 18 of the second microchannel 12b at the acoustic region 21b immediately downstream for detection of the analyte of interest in the second particle free fluid 28b.

Figure 7:
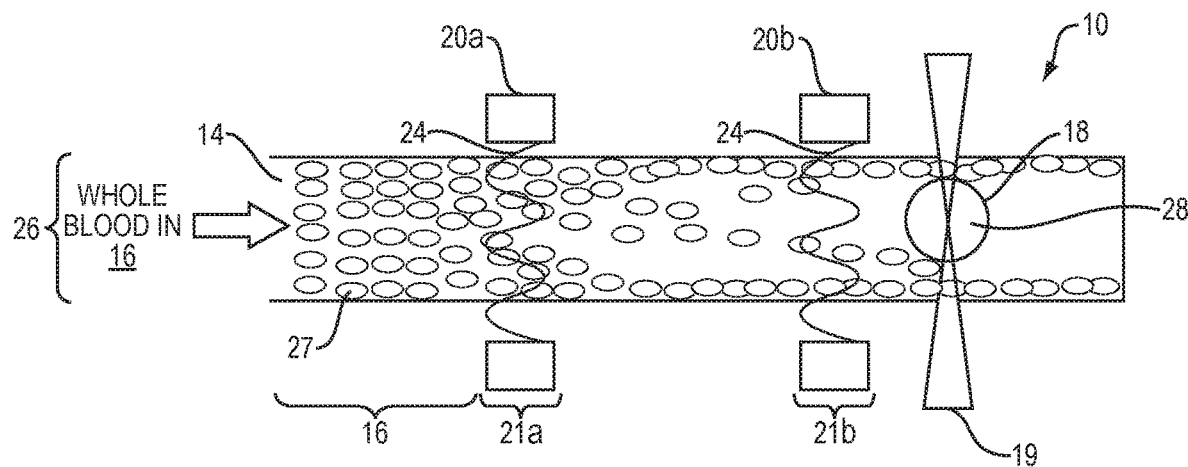
FIG. 7 schematically illustrates another embodiment of an acoustic configuration of the system according to the invention for detecting an analyte in a particle containing fluid in a channel by a detector located at a first detector region that is downstream from a first and a second acoustic transducer region.

FIG. 7 illustrates another embodiment of the acoustic configuration of the system 10 for particle partitioning, for example, RBCs in whole blood, and generation of a substantially particle-free fluid for analysis, such as plasma, for detection and analysis of a target analyte.

In the embodiment shown in FIG. 7, the complex fluid 16 is introduced via a sample port 14 in fluid communication with a microchannel 12. The complex fluid 16 fills and forms a fluid column 26 within the microchannel 12. Two or more acoustic transducers 20a, 20b, one for each acoustic region 21a, 21b, are configured in serial along a single microchannel 12.

In the embodiment illustrated in FIG. 7, the complex fluid 16 is separated twice, once at a first acoustic region 21a of the microchannel 12 and again a second time at a second acoustic region 21b of the microchannel 12 to obtain particle-free fluid 28 such as plasma in a single microchannel 12 for detection and analysis of a target analyte.

Analysis by the detector 19 at a location downstream from the acoustic regions 21n can be performed on the substantially particle-free fluid 28 while the fluid is flowing or arrested. Detectors 19 such as optical detectors/transmitters, or sensors such as traditional photometry detection apparatus, traditional fluorescence measurement systems, time resolved fluorescence measurement system, which usually includes LEDs, spectrometers, photodiodes and related optics, are located at a detector region in the microchannel for detection of the analyte of interest.

As described above, by releasing acoustic forces on the fluid sample, the partitioning of RBCs is reversible permitting the reconstitution of whole blood that may be collected in a downstream collector such as, for example, a tube, vessel, bag or chamber for collecting and holding whole blood.

Figure 8A:
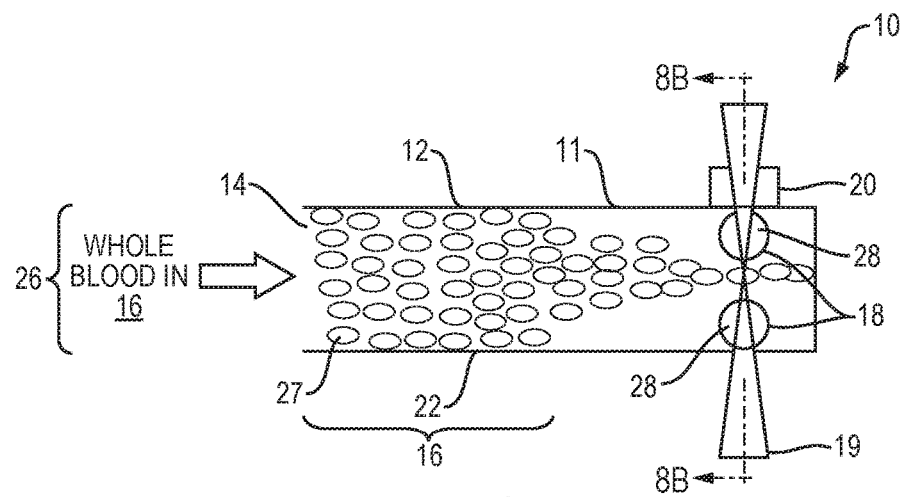
FIG. 8A schematically illustrates another embodiment of an acoustic configuration of the system according to the invention for detecting an analyte in a particle containing fluid in a channel by a detector located at a detector region and an acoustic transducer in which the acoustic force is introduced along a vertical direction in contrast to the systems of FIGS. 1-7 in which the transducer force is applied in a horizontal or transverse direction relative to the flow of fluid.

FIG. 8A illustrates another embodiment of the acoustic configuration of the system 10 for particle partitioning, for example, RBCs in whole blood, and generation of substantially particle-free fluid for fluid analysis such as plasma for detection and analysis of a target analyte.

In this embodiment, the complex fluid 16 is introduced via a sample port 14 in fluid communication with a microchannel 12. The complex fluid 26 fills and forms a fluid column 26 within the microchannel 12.

Figure 8B:
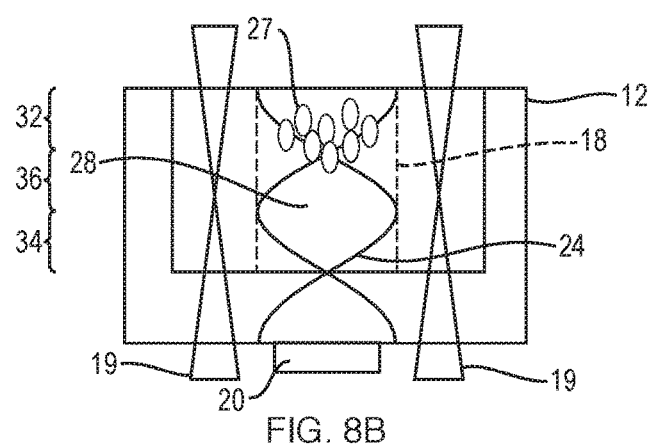
FIG. 8B schematically illustrates a cross-sectional view at 8b-8b of the acoustic force of the system illustrated in FIG. 8A applied to a column of blood for partitioning red blood cells from the plasma.

FIG. 8B illustrates that the acoustic force 24 is introduced along the vertical direction by an acoustic transducer 20. Particles, such as RBCs, are partitioned to the top layer 32 of the microchannel 12 and the substantially particle-free fluid 28, such as plasma, stays in the bottom 34 of the microchannel 12. By this configuration, the substantially particle-free fluid 28 is partitioned for analysis of a target analyte, such as hemoglobin, for the detection of hemolysis. Through acoustic configuration, the substantially particle-free fluid 28 can also be separated in the top layer 32, middle layer 36 or certain positions along the vertical axis of the microchannel 12.

Analysis by the detector 19 can be performed on the substantially particle-free fluid 28 while fluid is flowing or arrested. Detectors 19 such as optical detectors/transmitters, or sensors such as traditional photometry detection apparatus, traditional fluorescence measurement systems, time resolved fluorescence measurement system, which usually includes LEDs, spectrometers, photodiodes and related optics, are located at a detector region 18 in the microchannel for detection of the analyte of interest.

As described above, by releasing acoustic forces on the fluid sample, the partitioning of RBCs is reversible permitting the reconstitution of whole blood that may be collected in a downstream collector such as, for example, a tube, vessel, bag or chamber for collecting and holding whole blood.

Figure 9:
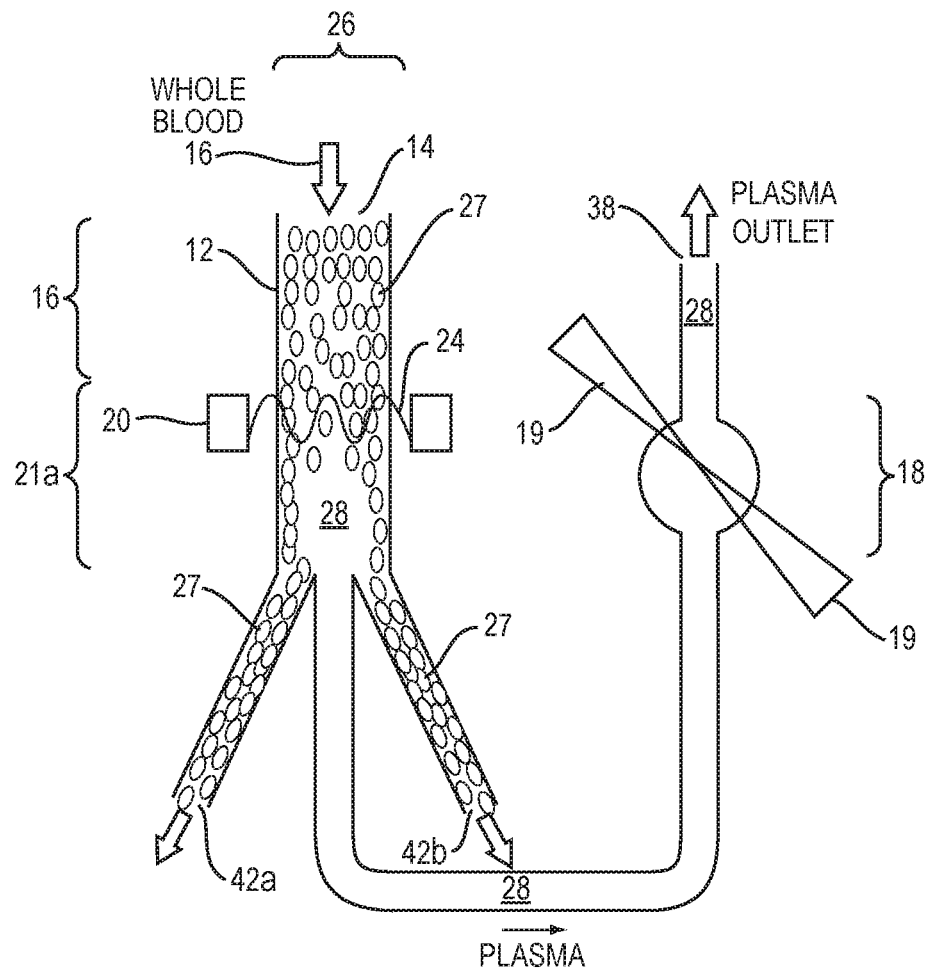
FIG. 9 schematically illustrates another embodiment of an acoustic configuration of the system according to the invention for detecting an analyte in a particle containing fluid in a channel by a detector located at a detector region, a transducer in a transducer region, and at least one port for harvesting red blood cells.

FIG. 9 illustrates another embodiment of the acoustic configuration system 10 for particle partitioning for example, RBCs in whole blood, and generation of a substantially particle-free fluid for fluid analysis such as plasma for detection and analysis of a target analyte.

In the embodiment illustrated in FIG. 9, the complex fluid 16 is introduced via a sample port 14 in fluid communication with a microchannel 12. The complex fluid 16 fills and forms a column 26 within the microchannel 12. The acoustic separation is performed at a first acoustic region 21a of the microchannel 12. Acoustic separation is a result of acoustic forces 24 transmitted by acoustic transducers 20 into the fluid column 26. The substantially particle-free fluid 28 flows in a column 26 to the detector region 18 for detection of hemolysis in a whole blood sample, while the particles 27 such as RBCs in the complex fluid 16 are partitioned and flow to an outlet port 42a, 42b.

Detector 19 such as optical detectors/transmitters, or sensors such as traditional photometry detection apparatus, traditional fluorescence measurement systems, time resolved fluorescence measurement system, which usually includes LEDs, spectrometers, photodiodes and related optics, are located at a detector region 18 in the microchannel 12 for detection of the analyte of interest. The particle-free fluid such as plasma flows through a plasma channel to a plasma outlet port 38 that is separate from particulate outlet ports 42a, 42b.

In yet another embodiment of the invention, multiple detector regions 18n in the microchannel 12 described in the above embodiments are associated with an acoustic device 20 and a detector 19 for analysis of multiple target analytes in a complex fluid such as whole blood, each target analyte being detected at one of the detector regions 18n.

What is claimed is:
1. A system comprising:
a channel to receive whole blood comprised of blood cells and plasma, the whole blood forming a fluid column in the channel;
a plurality of acoustic transducers including a first acoustic transducer to apply acoustic force to the fluid column in the channel to form a fluid layer in the channel, the fluid layer comprising the plasma, the fluid layer being substantially free of the blood cells, and the fluid layer being adjacent to a particle layer comprising the blood cells;

an optical detector that is aligned with the fluid layer to perform detection on the fluid layer to detect an analyte through measurement of the fluid layer;

wherein the first acoustic transducer is configured to apply the acoustic force at a first region of the channel;

wherein the plurality of acoustic transducers includes a second acoustic transducer configured to apply acoustic force at a different region of the channel than the first region; and wherein the optical detector comprises a spectrometer.

2. The system of claim 1, wherein the plurality of acoustic transducers are each configured to generate acoustic waves transverse to the fluid column, the acoustic waves for providing the acoustic force.

3. The system of claim 1, wherein the plurality of acoustic transducers are each configured to generate acoustic waves having a frequency in a range of 2 KHz to 2 GHz.

4. The system of claim 1, wherein the channel is among microchannels in the system.

5. The system of claim 1, wherein the plurality of acoustic transducers are configured to stop applying the acoustic force to allow the plasma and the blood cells to mix downstream of the optical detector.

6. The system of claim 1, wherein the first acoustic transducer is configured to apply the acoustic force to the fluid column upstream of the optical detector.

7. The system of claim 1, wherein the whole blood has a volume in a range of 1 microliter to 10 milliliters.

8. A method performed using the system of claim 1, the method comprising:

receiving the whole blood in the channel;

applying the acoustic force to the fluid column using the first acoustic transducer; and detecting the analyte using the optical detector.

9. The method of claim 8, wherein the acoustic force applied by the first acoustic transducer comprises acoustic waves applied transverse to the fluid column.

10. The method of claim 8, wherein the acoustic force applied by the first acoustic transducer is applied to the fluid column upstream of the optical detector.

11. A system comprising:

a channel to receive whole blood comprised of blood cells and plasma, the whole blood forming a fluid column in the channel;

a plurality of acoustic transducers including a first acoustic transducer to apply acoustic force to the fluid column in the channel to form a fluid layer in the channel, the fluid layer comprising the plasma, the fluid layer being substantially free of the blood cells, and the fluid layer being adjacent to a particle layer comprising the blood cells;

an optical detector that is aligned with the fluid layer to perform detection on the fluid layer to detect an analyte through measurement of the fluid layer;

wherein the first acoustic transducer is configured to apply the acoustic force at a first region of the channel;

wherein the plurality of acoustic transducers includes a second acoustic transducer configured to apply acoustic force at a different region of the channel than the first region; and wherein the analyte comprises free hemoglobin.

12. The system of claim 11, wherein the first acoustic transducer is configured to apply the acoustic force to the fluid column upstream of the optical detector.

13. The system of claim 11, wherein the acoustic force applied by the first acoustic transducer comprises an acoustic wave that forms two pressure nodes in the fluid column.

14. The system of claim 11, wherein the first acoustic transducer is configured to generate acoustic waves transverse to the fluid column, the acoustic waves for providing the acoustic force.

15. The system of claim 11, wherein the first acoustic transducer is configured to generate acoustic waves having with frequency in a range of 2 KHz to 2 GHz.

16. The system of claim 11, wherein the whole blood has a volume in a range of 1 microliter to 10 milliliters.

* * * * *